United States Patent [19]

Lagace et al.

[11] 4,400,299

[45] Aug. 23, 1983

[54] OXIDATIVE RECOVERY OF COBALT OXO CATALYSTS

[75] Inventors: Linda S. Lagace; Richard C. Miller; David A. Young, all of Baton Rouge, La.

[73] Assignee: Exxon Research & Engineering Co., Florham Park, N.J.

[21] Appl. No.: 333,693

[22] Filed: Dec. 23, 1981

[51] Int. Cl.[3] .................. B01J 31/40; B01J 31/20; C07C 27/22; C07C 45/50
[52] U.S. Cl. .................. 252/413; 252/414; 568/451; 568/909
[58] Field of Search ............ 252/416, 414, 413, 419, 252/420, 428, 443; 423/417; 568/451, 456, 909

[56] References Cited

U.S. PATENT DOCUMENTS

| 2,476,263 | 7/1949 | McKeever | 423/417 |
|---|---|---|---|
| 2,751,403 | 12/1952 | Mertzweiller | 260/414 |
| 3,265,468 | 4/1963 | Farkas et al. | 23/203 |
| 3,793,437 | 9/1971 | Takasu et al. | 423/417 |
| 3,941,848 | 7/1973 | Kummer et al. | 260/604 |
| 4,225,458 | 9/1980 | Huang et al. | 252/414 |
| 4,255,279 | 7/1979 | Spohn et al. | 252/413 |

FOREIGN PATENT DOCUMENTS

| 2451473 | 5/1976 | Fed. Rep. of Germany . | |
|---|---|---|---|
| 48-17594 | 5/1973 | Japan . | |
| 702221 | 1/1954 | United Kingdom . | |
| 1383658 | 2/1971 | United Kingdom . | |
| 1390898 | 8/1971 | United Kingdom . | |
| 2067914A | 8/1981 | United Kingdom | 252/413 |

OTHER PUBLICATIONS

R. Kummer et al., "New Hydroformylation Technology with Cobalt Carbonyls" *Homogeneous Catalysis-II*, Advances in Chemistry Series No. 132 (D. Forster et al.) pp. 19-26, (ACS 1973).
R. B. King, *Organometallic Synthesis*, vol. 1, p. 98, (Academic Press, 1965).
69 Chem. Abs. 95964d (1968), citing German Patent 1,272,911.
W. Hieber, W. Hübel, Zeitschr, Electrochem., 57, No. 4, pp. 235-243 (1953).
International Critical Tables, vol. 2, pp. 172-190 (McGraw-Hill, 1927).

*Primary Examiner*—P. E. Konopka
*Attorney, Agent, or Firm*—Jack B. Murray, Jr.

[57] ABSTRACT

According to one embodiment of the improved process of this invention, dicobalt octacarbonyl is produced in an olefinic medium by contacting an aqueous solution of a tetracarbonylcobaltate metal salt with an oxygen-containing gas in the presence of an olefinic extractant for dicobalt octacarbonyl to oxidize the tetracarbonylcobaltate anion to dicobalt octacarbonyl which is efficiently extracted into the olefinic phase, thereby producing an organic phase which can then be recovered and passed to a cobalt-catalyzed olefin hydroformylation reaction zone as source of at least a portion of the catalyst and olefin required in the olefin hydroformylation reaction to form the corresponding aldehydes. According to another aspect of this invention, an aqueous solution of tetracarbonylcobaltate metal salt is contacted with an oxygen-containing gas in the presence of gaseous carbon monoxide, and optionally also in the presence of an organic solvent for the dicobalt octacarbonyl, to efficiently oxidize the tetracarbonylcobaltate anion to dicobalt octacarbonyl.

16 Claims, 4 Drawing Figures

OXIDATIVE RECOVERY OF COBALT OXO CATALYSTS

CROSS-REFERENCE TO RELATED APPLICATION

This application is related to a commonly assigned application Ser. No. 333,734 filed Dec. 23, 1981, entitled "Improved Process for Recovery of Cobalt Oxo Catalysts".

BACKGROUND OF THE INVENTION

1. Field of the Invention

This invention in general relates to a process for recovering cobalt catalysts, and more specifically to an improved process for recovering and recycling cobalt oxo catalysts.

2. DESCRIPTION OF THE PRIOR ART

In the well known oxo process, olefins are hydroformylated by reaction with carbon monoxide and hydrogen, generally charged as syn gas mixtures, in the presence of a cobalt oxo catalyst in dissolved form to form a mixture of oxo aldehydes and alcohols. This oxo reaction is typically carried out at syn gas pressures of from about 1500 to 4500 psig and at temperatures of from about 65° to 230° C. Thereafter, the product mixture containing the alcohols and aldehydes is recovered and can then be treated by known means to hydrogenate the aldehydes to form additional quantities of the corresponding alcohols. These alcohols, in turn, are widely used as chemical intermediates in the manufacture of plasticizers, detergents, solvents and the like.

Prior to the hydrogenation step, the crude oxo reaction effluent, which contains dissolved cobalt catalysts, the product aldehyde and alcohol and reaction by-products together with any metallic contaminants, is generally treated to remove the dissolved cobalt catalyst, which then for reasons of economy must be recycled to the oxo reactor.

A wide variety of catalyst recovery/recycle processes have therefore been developed. U.S. Pat. No. 2,751,403 is directed to a process in which cobalt is removed from crude oxo products by extraction with an aqueous acid such as acetic acid to form an aqueous extract containing cobalt in both the cationic and anionic forms, viz., as the anion $[Co(CO)_4]^-$ and the corresponding cobalt salt, cobaltous bis-tetracarbonylcobaltate, $Co^{++}[Co(CO)_4^-]_2$. The aqueous extract is then subjected to oxidation with air or $O_2$ at 38° to 66° C. and at a pH of 5-6 with the addition of a higher molecular weight carboxylic acid salt, e.g., sodium oleate, to convert anionic cobalt to the $Co^{++}$ form and to achieve substantially quantitative recovery of the cobalt as a cobalt soap, e.g., cobaltous oleate, which was the desired catalytic species. The cobalt soap is then extracted into an organic liquid for recycle to the oxo reactor.

However, there has been continuous interest in other, lower cost alternatives to such expensive cobalt soaps, which during use are converted to other forms and have to be reconverted to the soap during the recycle process.

Another form of cobalt useful as oxo catalyst is dicobalt octacarbonyl, $Co_2(CO)_8$.

U.S. Pat. No. 3,265,468 discloses a process for producing $Co_2(CO)_8$ from an aqueous solution of an alkali metal carbonyl of cobalt (e.g., $NaCo(CO)_4$) by acidifying the solution with a mineral acid, followed by extraction, e.g., with toluene, to form an organic phase containing $Co_2(CO)_8$.

In U.S. Pat. No. 3,793,437, crude oxo effluent containing cobalt is contacted with an aqueous solution of metallic extracting agents, such as various metal salts and certain zeolites, in the presence of $H_2$ and CO to form an aqueous salt of carbonyl cobaltate which is subsequently decomposed with an organic acid or a mineral acid to a water-soluble cobalt hydridocarbonyl. The aqueous solution containing the cobalt hydridocarbonyl is then heated in the present of CO and a water-immiscible organic solvent to form dicobalt octacarbonyl which is extracted into the organic solvent. After further treatment (e.g., drying, dilution or concentration), the organic solvent can be recycled to the oxo reactor. The patentees indicate that the thus-recovered cobalt carbonyl is sensitive to oxygen or oxidizing agents and must be protected from such oxidants as by degassing or by replacement of the ambient atmosphere with inert gas.

R. Kummer, et al., "New Hydroformylation Technology with Cobalt Carbonyls," *Homogeneous Catalysis—II*, Advances in Chemistry Series No. 132 (D. Forster et al.), pp. 19–26 (A.C.S. 1973) relates to a BASF process in which crude oxo product is demetalled at 120° C. and 10 atm. with air and an aqueous formic acid/cobaltous formate solution, and the resulting aqueous $Co^{++}$ formate solution is reacted with CO and $H_2$ to preform anionic cobalt, $Co(CO)_4^-$, in the solution, which is then subjected to an olefin extraction to give an olefin phase containing cobalt as either $Co_2(CO)_8$ or (at low CO pressure) $Co_4(CO)_{12}$. Kummer et al. describes the crude oxo product demetalling step by the following equation (I):

$$Co_2(CO)_8 + O_2 + 4H_3O^+ + 4HCOO^- \rightarrow$$
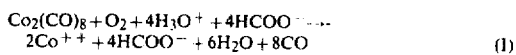
$$2Co^{++} + 4HCOO^- + 6H_2O + 8CO \quad (1)$$

The authors point out that the resulting aqueous phase contains all the cobalt and that only water-soluble $Co^{++}$ compounds are formed.

German Pat. No. 1,272,911 to BASF, as cited at 69 Chem. Abs. 95964d (1968), describes the demetalling of a crude oxo product at 116° C. and 30 atm. with air, acetic acid, water and a recycled $Co^{++}$ salt solution, using a residence time in the demetalling zone of 3 seconds, to give an organic phase containing practically no cobalt.

The following BASF patents relate to similar processes: U.S. Pat. No. 3,941,848; British Pat. Nos. 1,383,658 and 1,390,898; and German Offenlegungschrift No. 2,451,473 (1976).

U.S. Pat. No. 4,255,279 contacts a crude oxo effluent in a first step with an aqueous $Co^{++}$ salt of an organic or inorganic acid to extract cobalt into the aqueous phase. After separation from the thus-treated crude oxo product, the aqueous phase, which contains cationic and anionic cobalt, $Co^{++}$ and $Co(CO)_4^-$, is treated with syn gas to preform additional $Co^{++}$ into the anionic, $Co(CO)_4^-$, form. The preformed effluent is then contacted with an organic solvent to extract cobalt carbonyls therefrom into the organic phase for ultimate recycle to the oxo reactor. The treated crude oxo product obtained from the first step still contains some cobalt in an oil-soluble form, e.g., dicobalt octacarbonyl, and is further demetalled by treatment at 65° to 93° C. with an aqueous organic or inorganic acid and oxygen to oxidize the cobalt to a water-soluble form, e.g., $Co^{++}$ salt of the selected acid. The patentees indicate that substantially all of the cobalt is thereby separated from the organic layer, resulting in an oxo product containing cobalt in a concentration of about 10 ppm or less.

Japanese Patent Publication 73/17,594 (May 30, 1973) oxidizes a cobalt hydrocarbonyl water-soluble metal salt (e.g., $NaCo(CO)_4$ or $Co[Co(CO)_4]_2$) in aqueous solution with air or $O_2$ to form dicobalt octacarbonyl solids, followed by extraction thereof using an organic solvent or raw material olefin or their mixture. Alternatively, the patentees indicate that the organic solvent can be added in the oxidation step to extract the dicobalt octacarbonyl directly into the organic solvent layer.

In R. B. King, *Organometallic Synthesis*, vol. 1, p. 98 (Academic Press 1965), it is indicated that $Co_2(CO)_8$ crystals are soluble in organic solvents; are unstable to both thermal decomposition and air oxidation; and rapidly lose CO at 50° C. to form $Co_4(CO)_{12}$ and ultimately cobalt metal. On exposure to air for several minutes, $Co_2(CO)_8$ crystals are said to be oxidized to a $Co^{++}$ derivative, which is presumed to be either the oxide or the carbonate. Also, $Co_2(CO)_8$ crystals, when isolated by crystallization from organic solvents, are said to be pyrophoric if obtained as finely divided crystals. A preparatory procedure is therefore suggested in which cobalt (II) acetate tetrahydrate is reacted at 160°–180° C. with CO and $H_2$ to form acetic acid and $Co_2(CO)_8$ crystals, which are isolated by filtration under $N_2$.

W. Hieber and W. Hübel, Zeitschr. Elektrochem. 57, no. 4; pp. 235–243 (1953) indicate that solutions of cobalt carbonyl hydride are very sensitive to oxidizing agents and that dimeric cobalt carbonyl flakes are immediately formed from even minute traces of atmospheric oxygen (see Section I, paragraph 2).

SUMMARY OF THE INVENTION

According to one embodiment of the improved process of this invention, dicobalt octacarbonyl is produced in an olefinic medium by contacting an aqueous solution of a tetracarbonylcobaltate metal salt with an oxygen-containing gas in the presence of an olefinic extractant for dicobalt octacarbonyl to oxidize the tetracarbonylcobaltate anion to dicobalt octacarbonyl which is efficiently extracted into the olefinic phase, thereby producing an organic phase which can then be recovered and passed to a cobalt-catalyzed olefin hydroformylation reaction zone as source of at least a portion of the catalyst and olefin required in the olefin hydroformylation reaction to form the corresponding aldehydes. It has been surprisingly found, contrary to the teachings of the prior art, that olefins can be employed as the extractant liquid in the oxidation zone without formation of economically disadvantageous olefin-oxidation by-products.

According to another aspect of the process of this invention, it has been found that greatly improved yields of dicobalt octacarbonyl can be obtained by contacting an aqueous solution of tetracarbonylcobaltate metal salt with an oxygen-containing gas in the presence of gaseous carbon monoxide, and optionally also in the presence of an organic solvent for the dicobalt octacarbonyl, to efficiently oxidize the tetracarbonylcobaltate anion to dicobalt octacarbonyl. If the oxidation is effected in an aqueous medium, the resulting aqueous slurry of dicobalt octacarbonyl can be contacted with an organic solvent to form an organic phase containing dicobalt octacarbonyl suitable for recycle to hydroformylation. Alternatively, if the oxidation is effected in the presence of an organic solvent, an organic phase containing dicobalt octacarbonyl can be recovered from the oxidation reaction zone for recycle to the hydroformylation reaction.

According to another embodiment of this invention, crude oxo products produced by the cobalt-catalyzed hydroformylation of olefins and containing dissolved cobalt catalyst together with hydroformylation products are contacted in a low pressure extraction zone with an aqueous solution of a $Co^{++}$ salt of an organic or inorganic acid to form an aqueous phase containing water-soluble cobalt values, i.e., $Co^{++}[Co(CO)_4^{-}]_2$ and $Co^{++}$ salts of said acid and a treated oxo product depleted in dissolved cobalt values. The aqueous phase thus obtained is the contacted with an $O_2$-containing gas to form dicobalt octacarbonyl from the cobalt values dissolved therein. The resulting aqueous slurry is next contacted in a separate extraction zone with an organic solvent for said dicobalt octacarbonyl to provide an extract comprising an organic phase containing dicobalt octacarbonyl suitable for recycle to said hydroformylation. An aqueous raffinate containing dissolved $CO^{++}$ salt of said acid and substantially free of dicobalt octacarbonyl is recovered from the high pressure extraction zone and at least a portion thereof is contacted with high molecular weight fatty acid anions and organic solvent therefore to form the corresponding $Co^{++}$ salt of said higher fatty acid. The resulting organic phase, which comprises the high molecular weight fatty acid $Co^{++}$ salt and organic solvent, can be recycled to the hydroformylation to provide additional catalyst therein.

In another embodiment, the organic phase containing organic solvent and the higher fatty acid $Co^{++}$ salt is passed to the extraction zone as the feed of organic solvent thereto. In this embodiment, the organic extract recovered from the extraction zone comprises the organic solvent, dicobalt octacarbonyl, and the $Co^{++}$ higher fatty acid salt and is recycled to the hydroformylation zone.

In accordance with yet further embodiments, the foregoing oxidative treatments of the aqueous phase withdrawn from the low pressure extraction zone is conducted simultaneously with the extraction in the same reaction vessel.

DETAILED DESCRIPTION OF THE INVENTION

Figure 1:
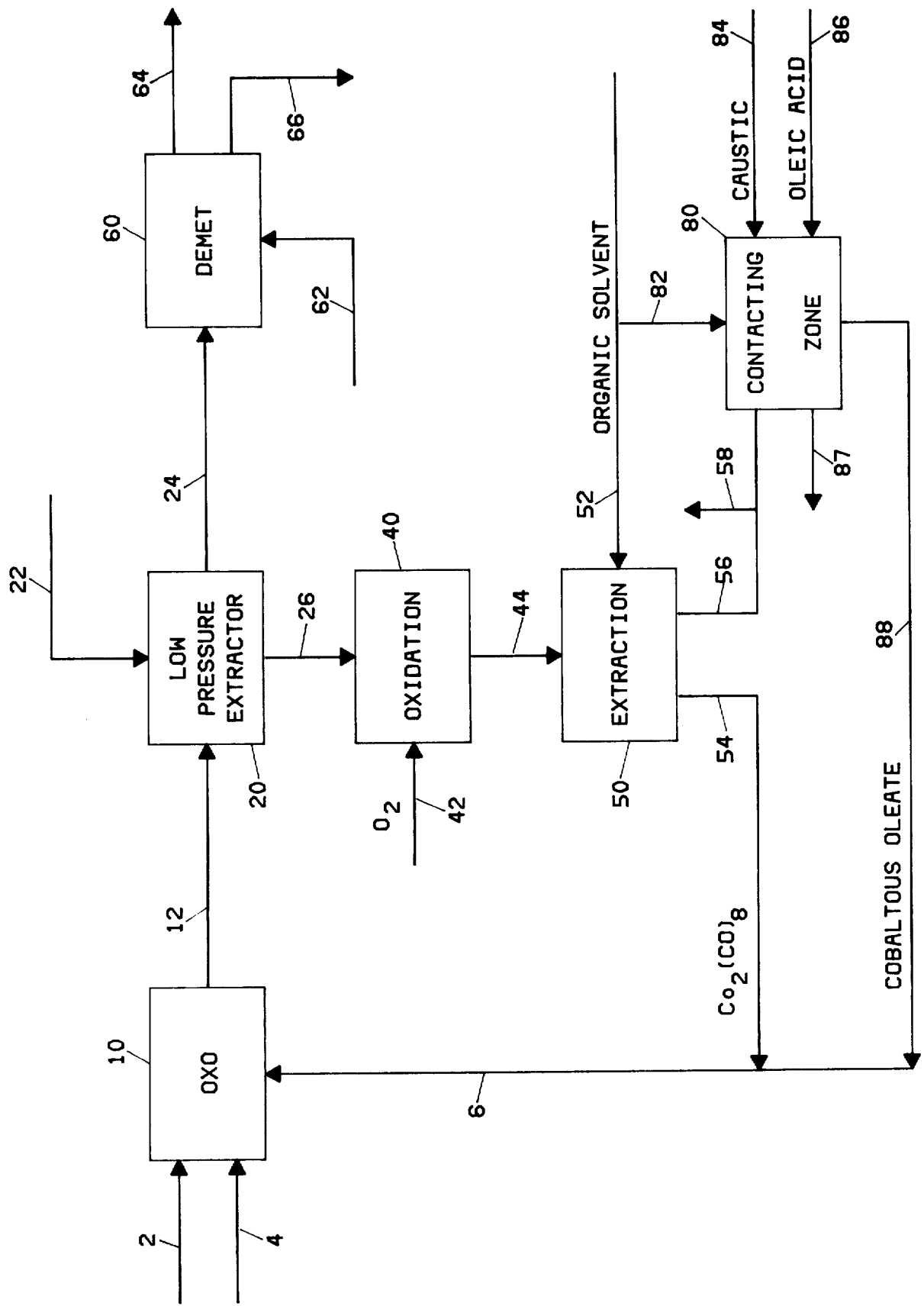
FIG. 1 is a diagrammatic illustration of one embodiment of the process of this invention.

According to one embodiment of this invention, an aqueous solution of a tetracarbonylcobaltate salt is contacted with an $O_2$-containing gas in a reaction zone in the presence of a free organic or inorganic, water-soluble acid and in the presence of an olefinic liquid extractant for $Co_2(CO)_8$ to form an olefinic phase containing dicobalt octacarbonyl and substantially free of oxidation by-products of the olefinic extractant, and an aqueous phase substantially free of $Co_2(CO)_8$.

The tetracarbonylcobaltate salt in the aqueous phase can be represented in its dissociated form as $M^{+n}[Co(CO)_4^-]_n$, wherein "M" is a cation and "n" is an integer corresponding to the valence of "M". Thus, "M" can comprise a member selected from the group consisting of Co, alkali and alkaline earth metal, Fe, Cu, Mo, Ni, Al, Zn, $NH_4^+$, $H_3NR^+$, $H_2NR_2^+$, $HNR_3^+$, $NR_4^+$, and $PR_4^+$ wherein "R" is alkyl of 1 to 20 carbon atoms, aryl of 6 to 18 carbon atoms, alkaryl and aralkyl of 7 to 18 carbon atoms and heterocyclic derivatives of the foregoing aromatic groups. Exemplary tetracarbonylcobaltate metal salts, therefore, are $NaCo(CO)_4$, $Co[Co(CO)_4]_2$, $KCo(CO)_4$, $Mg[Co(CO)_4]_2$, $Mg[Co(CO)_4]_2$, $Al[Co(CO)_4]_3$, $Cu[Co(CO)_4]_2$, and the like of which $Co[Co(CO)_4]_2$ is especially preferred.

While we do not wish to be bound by any theory, it is believed the reaction forming $Co_2(CO)_8$ in the oxidation zone can be illustrated by the following expression in which acetic acid is employed as an illustrative acid and cobaltous tetracarbonylcobaltate is the illustrative reactant salt:

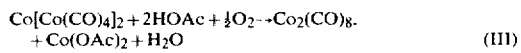

$$Co[Co(CO)_4]_2 + 2HOAc + \tfrac{1}{2}O_2 \rightarrow Co_2(CO)_8 + Co(OAc)_2 + H_2O \quad \text{(III)}$$

Suitable organic or inorganic acids will be water soluble in an amount of at least about 0.04 gram per gram of water at 25° C. Illustrative of suitable organic or inorganic acids are monocarboxylic acids having from 1 to 4 carbon atoms per molecule (which are preferred), dicarboxylic acids having from 2 to 5 carbon atoms per molecule, and the like. Exemplary of such acids, therefore, are alkanoic acids such as formic, acetic, propionic, butyric, isobutyric, propionic, oxalic, malonic, succinic, and the like. The quantity of acid charged to the oxidation zone can vary but is preferably from about 1 to 50, and more preferably 2 to 25, times the moles stoichiometrically required to react with the quantity of the bis-tetracarbonylcobaltate metal salt introduced to the oxidation zone.

The aqueous feed to the oxidation zone will generally contain the tetracarbonylcobaltate metal salt in a concentration of from about 0.5 to 25 wt. %, preferably from about 1 to 10 wt. %, calculated as $Co(CO)_4^-$, and the selected inorganic or organic acid in a concentration of from about 0.2 to 10 wt. %. However, these concentration ranges are not critical and can vary widely.

The olefin fed to the oxidation zone can comprise any carbon compound containing olefinic linkages. Amenable to the reaction are long and short chained olefinic compounds, depending upon the type aldehydes desired. Not only olefins, but most organic compounds possessing at least one non-aromatic carbon-carbon double bond may be reacted by this method. Thus, straight and branch-chained olefins and diolefins such as propylene, butylene, pentene, hexene, heptane, butadiene, pentadiene, styrene, olefin polymers such as di- and tri-isobutylene and hexene and heptene dimers, polypropylene, olefinic fractions from the hydrocarbon synthesis process, steam cracking or catalytic cracking operations, and other sources of hydrocarbon fractions containing olefins may be used as starting material, depending upon the nature of the final product desired. Also suitable are olefins bearing functional groups such as $—C\equiv N$, $—OH$, -halide and the like which do not adversely affect the hydroformylation reaction. Illustrative of such functionally substituted olefins are acrylonitrile, alkyl alcohol, alkenyl esters of acrylic acid, acrylic acid, vinyl halides and the like. Preferred are olefins having from 4 to 20 carbon atoms, more preferably from 6 to 12 carbon atoms, (such as butenes, pentenes, hexenes, heptenes, octenes, decenes, dodecenes and the like), and aryl-substituted alpha-olefins (such as styrene, stilbene, divinylbenzenes and the like).

The selected liquid olefinic extractant preferably corresponds to the olefin to be hydroformylated in the subsequent hydroformylation reaction, and is preferably used in an amount of from about 0.1 to 10 volumes per volume of aqueous feed introduced to the oxidation zone.

The aqueous feed to the oxidation zone can also contain water-soluble metal salts of any of the above inorganic or organic acids, in which the salt's cation can comprise any of the above "M" cations and preferably corresponds to the metal cation associated with the tetracarbonylcobaltate metal salt. The concentration of these inorganic or organic metal salts is not critical and will vary depending on the precise metal cation, the acid anion, and other factors. For example, $Co^{++}$ salts of such organic and inorganic acids, when present, will generally be in a concentration of from about 0.5 to 4.0 wt. %, calculated as elemental cobalt, based on the amount of water in the oxidation zone.

The source of the aqueous solution containing the tetracarbonylcobaltate metal salt and free acid is not critical. A preferred aqueous stream for oxidation in accordance with this invention is the aqueous effluent from a pressure extraction of crude olefin-hydroformylation reaction products, as will be described in more detail below. The oxidation reaction can be performed in a continuous, semi-continuous or batchwise manner, with the components being introduced thereto separately or in any admixture. The temperature employed in the oxidation zone can range from about 0° to 90° C., and preferably from about 10° to 50° C. Pressures are not critical and can vary from about 15 to 1500 psig, more preferably from about 50 to 500 psig. However, pressures outside this range are also suitable. The molecular oxygen can be introduced in any convenient form, such as a gaseous feed of pure oxygen or as oxygen admixed with inert gases such as nitrogen, argon and the like. Atmospheric air is entirely suitable for this oxidation. The residence time of the aqueous mixture in the oxidation zone can also vary widely, and will generally range from about 5 seconds to 1 hour, and preferably from about 0.5 to 15 minutes.

The effluent from the oxidation zone comprises organic and aqueous phases which can be separated and recovered using conventional equipment and techniques. The aqueous phase is depleted in carbonylcobaltate values and is substantially free of $Co_2(CO)_8$. The olefinic phase, which will typically contain from about 0.1 to 11 wt. %, preferably from about 0.5 to 6 wt. %, dissolved $Co_2(CO)_8$, has been found to be substantially free of oxidation by-products formed by reaction of the olefin extractant and $O_2$ in the oxidation zone. The recovered olefinic phase is therefore suitable as feed to a cobalt-catalyzed olefin hydroformylation reaction to supply at least a portion of the homogeneous cobalt catalyst required therein.

Reference is now made to the accompanying drawings, wherein like numerals refer to the same or similar elements. Referring first to FIG. 1, an olefin feed is introduced via conduit 2 to oxo reactor 10 to which is also fed a mixture of CO and $H_2$ (synthesis gas) via conduit 4 and an organic liquid containing dissolved cobalt catalyst via conduit 6. The oxo reaction is conventional and typically employs a temperature of from about 65° to 240° C. and syn gas pressures of from about 1500 to 4500 psig.

The olefin fed to the oxo reactor 10 can comprise any carbon compound containing olefinic linkages, described above as useful in the oxidation zone to extract the $Co_2(CO)_8$. Thus, straight and branch-chained olefins and diolefins such as propylene, butylene, pentene, hexene, heptene, butadiene, pentadiene, styrene, olefin polymers such as di- and tri-isobutylene and hexene and heptene dimers, polypropylene, olefinic fractions from the hydrocarbon synthesis process, steam cracking or catalytic cracking operations, and other sources of hydrocarbon fractions containing olefins may be used as starting material, depending upon the nature of the final product desired.

Also suitable are olefins bearing functional groups such as $-C\equiv N$, $-OH$, halide and the like which do not adversely affect the hydroformylation reaction. Illustrative of such functionally substituted olefins are acrylonitrile, allyl alcohol, alkenylesters of acrylic acid, acrylic acid, vinyl halides and the like. Preferred are olefins having from 2 to 20 carbon atoms (such as ethylene, propylene, butenes, pentenes, hexenes, heptenes, octenes, decenes, dodecenes and the like) and aryl-substituted alpha-olefins (such as styrene, stilbene, divinylbenzenes and the like).

Crude oxo product is withdrawn from oxo reactor 10 via conduit 12 and comprises dissolved cobalt catalyst, unreacted olefin, hydroformylation product and hydroformylation by-products. The dissolved catalyst species in the oxo reactor, and hence in the crude oxo products, is considered to be hydrido cobalt tetracarbonyl, $HCO(CO)_4$, which is in equilibrium with hydrido cobalt tricarbonyl, $HCo(CO)_3$, according to "Organic Synthesis via Metal Carbonyls," Wender and Pino, Inter Science Publishers, volume I, pages 249-251. The crude oxo product will generally contain cobalt in an amount of from about 0.05 to 3.0 wt. %, calculated as elemental cobalt. The concentration of aldehyde in the crude oxo product is not critical but will generally vary from about 40 to 75 wt. %.

The crude oxo product is introduced via conduit 12 into first extraction zone 20 wherein the crude oxo product is contacted with an aqueous solution containing a $Co^{++}$ salt of an organic or inorganic acid to form a treated oxo product depleted in dissolved cobalt values and an aqueous phase containing $Co^{++}[Co(CO)_4^-]_2$ together with an excess $Co^{++}$ salt of said acid. While the conditions employed in this first extraction zone 20 can vary widely, the extraction will generally be performed at a temperature within the range of from about 10° to 95° C., and preferably from 50° to 90° C., and at a pressure of from about atmospheric to about 200 psig, preferably from about 20 to 100 psig. The organic or inorganic acid which forms the anion of the $Co^{++}$ salt introduced via conduit 22 can comprise any organic or inorganic acid the cobalt salt of which is is water soluble in an amount of at least about 0.04 gram per gram of water at 25° C. Illustrative of suitable organic or inorganic acids are monocarboxylic acids having from 1 to 4 carbon atoms per molecule, dicarboxylic acid having from 2 to 5 carbon atoms per molecule, and the like. Thus, illustrative of suitable cobalt salt are cobaltous acetate, formate, propionate, butyrate and isobutyrate, and cobaltous oxalate, malonate, succinate and glutarate and mixtures thereof. The concentration of the $Co^{++}$ salt of said organic or inorganic acid in the aqueous medium introduced via conduit 22 is not critical but will generally range from about 0.5 to 4.0 wt. %, calculated as elemental cobalt. The quantity of said aqueous extractant which is introduced via conduit 22 can also vary widely, and the aqueous extractant will generally be used in an amount of from about 0.005 to 0.5, and preferably from about 0.02 to 0.16 volume of said aqueous extractant per volume of crude oxo product introduced via conduit 12.

Preferably, the crude oxo product is extracted in zone 20 in the presence of an inert gas such as nitrogen or synthesis gas (i.e., any mixture of CO and $H_2$). When the extraction in low pressure extractor 20 is performed in the presence of synthesis gas, the synthesis gas preferably has a composition of from about 40 to 60 vol. % CO and from about 40 to 60 vol. % $H_2$. The extraction of the crude oxo product in zone 20 is preferably conducted for a time sufficient to extract a major amount, i.e., more than ½, and preferably at least about 90%, of the cobalt values dissolved in the crude oxo product, calculated as elemental cobalt.

Following the treatment in extraction zone 20, the aqueous and organic phases thus obtained are separated as by settling employing conventional equipment. The organic phase comprises the treated oxo product depleted in dissolved cobalt values and now contains, e.g., up to about ⅓ of the original amount of cobalt. This treated oxo product can be passed via conduit 24 into demetalling zone 62 wherein it is contacted at a temperature of from 35° to 95° C. with oxygen or air, acetic acid or other suitable acid and water which is introduced thereto via conduit 62, thereby converting the remaining cobalt values into the aqueous soluble cobaltous salt of the acid, e.g., cobaltous acetate. The organic and inorganic acid suitable for use in demetalling zone 60 can comprise any of the organic or inorganic acids which are useful (as described above) in the aqueous extractants introduced to zonde 20 via conduit 22.

From demetalling zone 60 there are withdrawn organic and aqueous phases, obtained as by settling, employing conventional equipment. The organic phase which is withdrawn via conduit 64 comprises the oxo product substantially free of dissolved cobalt values and generally less than about 10 ppm Co. The aqueous phase withdrawn from demetalling zone 60 via conduit 66 comprises an aqueous mixture containing the dissolved cobaltous salt and can be passed (after addition of make-up cobaltous acid salt, if needed) to conduit 22 as the aqueous extractant medium fed to first extraction zone 20. The make-up cobalt may be needed because some thermal degradation of the hydrido cobalt tetracarbonyl may occur in the process since it does not operate at 100% efficiency. Depending on operating conditions in oxo reactor 10, the amount of makeup that must be added from an outside source typically ranges from 0 to 10 wt. % of the total cobalt employed. The addition of the water-soluble cobaltous acid salt is a simple and convenient way of accomplishing the required make-up of cobalt values.

The aqueous phase withdrawn from low pressure extraction zone 20 via conduit 26 comprises an aqueous solution containing $Co[Co(CO)_4]_2$, and any excess cobaltous salt of the selected acid, e.g., cobalt acetate, in addition to free acid, e.g., acetic acid. This solution is introduced via conduit 26 into oxidation zone 40 wherein the aqueous phase is contacted with molecular $O_2$-containing gas introduced thereto via conduit 42 in order to form dicobalt octacarbonyl therein. Any of the above-described acids whose cobaltous salts are useful in the aqueous extractant fed via conduit 22 to low pressure extractor 20 are also suitable for use in the oxidation zone. Typically, the acid will correspond to the cobaltous acid salt used in the extraction zone 20. Exemplary of such acids, therefore, are alkanoic acids such as formic acid, acetic, propionic, butyric, isobutyric, propionic and the like. The quantity of acid charged to oxidation zone 40 can vary but is preferably from about 1 to 50, and more preferably 2 to 25, times the moles stoichiometrically required to react with the quantity of cobaltous bis-tetracarbonylcobaltate introduced to the oxidation zone 40 via conduit 26.

The aqueous phase introduced via conduit 26 will generally contain from about 0.5 to 25, preferably from 1 to 10 wt. % cobaltous bis-tetracarbonylcobaltate, calculated as elemental cobalt, and can also contain cobaltous salts of the inorganic or organic acid selected for use in extraction zone 20. When present, such cobaltous inorganic and organic acid salts will be present in an amount generally from about 0.2 to 10 wt. %, preferably from about 1 to 3 wt. %, in the case of cabaltous alkanoates (e.g., acetate).

The oxygen-containing gas can be contacted with the aqueous phase in zone 40 in any convenient manner, such as by gas sparging, or by use of suitable agitation devise to accelerate absorption of the oxygen into the liquid phase for reaction, or a combination thereof.

The temperature employed in zone 40 can range from about 0° to 90° C., and preferably from about 10° to 50° C. Pressures in zone 40 are not critical and can vary from about 15 to 1500 psig., more preferably from about 50 to 5000 psig. However, the pressures outside this range are also suitable. The molecular oxygen can be introduced in any convenient form, such as a gaseous feed of pure oxygen or as oxygen admixed with inert gases such as nitrogen, argon and the like. Atmospheric air is entirely suitable for this oxidation. The residence time of the aqueous mixture in oxidation zone 40 can also vary widely, and will generally range from about 5 seconds to 1 hour, and preferably from about 0.5 to 15 minutes.

The effluent from oxidation zone 40, comprises an aqueous slurry of solid dicobalt octacarbonyl and contains dissolved cobaltous acid salt, generally in an amount of from about 0.5 to 5.0 wt. % solid $Co_2(CO)_8$ and from about 0.2 to 10.0 wt. % dissolved cobaltous acid salt, based on the weight of the total aqueous slurry. This slurry is then passed via conduit 44 from oxidation zone 40 to second extraction zone 50 wherein an extraction is performed in the presence of an organic solvent for the dicobalt octacarbonyl, introduced thereto via conduit 52. The organic extracting liquid can be an olefinic or non-olefinic liquid and may be selected from U.O.P. olefins (defined in U.S. Pat. No. 4,078,132), the feed olefins (e.g., a portion such as 10% of the olefin feed to reactor 10), hydroformylation product from any stage, the heavy oxygenated fraction (HOF) bottoms from the distillation of demetalled oxo alcohol product, or other suitable solvents alone or in combination. Other illustrative suitable organic solvents are those which are inert to the dicobalt octacarbonyl and which do not interfere with the desired hydroformylation reaction on recycle to oxo reaction 10, including for example saturated hydrocarbons, aromatic hydrocarbons, acetals, ethers, esters and mixtures comprising two or more of these solvents. Saturated hydrocarbons include, for example, methane, ethane, propane, butane, pentane, hexane, heptane, octane, nonane, decane, gasoline, cyclopentane, cyclohexane and decaline; aromatic hydrocarbons include, for example, benzene, toluene, xylene, tetraline, naphthalene, and methylnaphthalene; acetals include, for example, reaction products between the aldehydes and alcohols formed in the hydroformylation such as the bis-butylacetal of butyraldehyde, bis-decylacetal of decanal and the like; ethers include, for example, diethyl ether, di-i-propylether, d-n-butylether, di-i-butylether, ethylene glycol dimethyl ether and ethylene glycol diethyl ether, and esters include, for example, methyl acetate, ethyl formate, propyl acetate and butyl acetate.

The conditions employed in second extraction zone 50 can vary widely. The temperature of extraction will generally range from about 0° to 90° C., preferably from about 10° to 50° C., the pressure will generally range up to about 4500 psig, preferably from about 1 to 1000 psig, more preferably from about 15 to 300 psig, and the quantity of organic solvent employed will generally range from about 0.1 to 10 volumes of the organic solvent per volume of the aqueous mixture introduced to zone 50 via conduit 44. The extraction in zone 50 can be effected in the presence of mixtures of CO and hydrogen (e.g., syn gas having from 40 to 60% CO and from 60 to 40% $H_2$), and inert gases such as nitrogen, methane (e.g., natural gas) and the like. Preferably, oxygen is excluded from second extraction zone 50 when the temperature of extraction exceeds about 90° C., more preferably exceeds about 50° C.

The aqueous and organic phases are separated using conventional equipment and techniques, and the organic phase, which comprises the organic solvent containing dissolved dicobalt octacarbonyl, can be passed via conduit 54 to conduit 6 as recycle catalyst feed to oxo reactor 10. Ths recycled organic phase will generally contain from about 0.1 to 11 wt. % dissolved $Co_2(CO)_8$, and preferably from about 3 to 8 wt. % dissolved $Co_2(CO)_8$.

The organic phase can also contain other cobalt carbonyls and complexes, such as $CO_4(CO)_{12}$, $\pi$-olefin cobalt tetracarbonyl and tricarbonyl complexes, and alkyl and acyl cobalt tetracarbonyls and tricarbonyls wherein the foregoing olefin, alkyl and acyl groups are derived from the olefin fed to the hydroformylation.

The aqueous phase, containing the dissolved cobaltous acid salt and substantially free of $Co_2(CO)_8$, is withdrawn from extraction zone 50 via conduit 56 and a portion thereof can be recycled, if desired, via conduit 58 to conduit 22 (together with make-up cobaltous acid salt, if necessary) as a portion or all of the aqueous extractant introduced to zone 20. If desired, the aqueous phase in conduit 56 can also be passed to conduit 26 and/or to conduit 62 to aid in the final demetalling step in zone 60.

Generally, from about 40 to 80 wt. % of the aqueous solution in conduit 56 will be recycled: via conduit 58, and therefore from about 60 to 20 wt. % will be passed to contacting zone 80, as will be discussed below. It will be understood that the aqueous solution containing cobaltous acid salt recycled via conduit 58, as well as the aqueous solution withdrawn from demetalling zone 60 via conduit 66, can be passed to suitable storage vessel (not shown) which can serve as intermediate storage of the aqueous extractant ultimately intended for recycle to conduits 22, 26 or 62, as described above. It should be noted that there is no discarding of the circulating stream, which both conserves cobalt and avoids pollution. However, if excess water accumulates, it can be removed by withdrawing a sidestream (not shown) from such storage vessel, which sidestream can then be treated to evaporate a portion of the water therefrom and to return the thus-concentrated stream to the storage vessel.

The portion of the aqueous raffinate in conduit 56, which is not recycled as above described via conduit 58, is passed to contacting zone 80 wherein this aqueous raffinate, which contains dissolved cobaltous salt of a water-soluble acid (such as cobaltous acetate), is contacted with a higher molecular weight fatty acid (e.g., oleic acid), which is introduced thereto via conduit 86, an organic solvent for the higher fatty acid which is introduced thereto via 82 and an alkaline reacting agent which is introduced thereto via conduit 84. The alkaline reacting agent, e.g., caustic, reacts with the added higher fatty acid to form the corresponding (e.g., sodium) salt which then reacts with the cobaltous values introduced via the aqueous raffinate to form a cobaltous salt of the higher fatty acid which is extracted by the organic solvent.

While not wishing to be bound thereby, it is believed the reactions in zone 80, employing cobaltous acetate, caustic and oleic acid as exemplary feeds, can be illustrated by the following equation (IV):

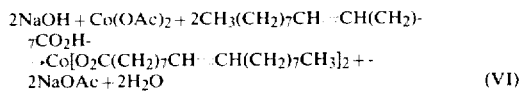

Thus, the organic phase containing the cobaltous higher fatty acid salts can be withdrawn from contacting zone 80 via conduit 88 and recycled to conduit 6. The aqueous phase thereby formed can be withdrawn via conduit 87 and passed to waste.

The higher molecular weight fatty acids which are introduded to zone 80 can comprise fatty acids which are substantially insoluble in water, i.e., possess a water solubility of less than about 0.1 grams of acid per liter of water at 25° C. Illustrative of suitable higher fatty acids, therefore, are stearic acid, oleic acid, palmitic acid, naphthinic acid, decanoic acid, 2-ethyl-hexanoic acid and the like. Preferred higher fatty acids are oleic acid and by-product acids recovered from hydroformylation effluent, e.g., alkanoic acids having a carbon skeleton equivalent to the product aldehyde.

The fatty acid should be introduced via conduit 86 in an amount sufficient to provide the moles of acid required to react with the moles of cobaltous cations introduced with the aqueous raffinate to zone 80. Typically, the higher fatty acid will be introduced in an amount sufficient to provide from about 2.0 to 2.2 moles of the higher fatty acid per mole of cobaltous cations thus introduced to zone 80.

The alkaline reacting agent introduced via conduit 84 can comprise any basically reacting material which will react with the selected higher fatty acid to liberate water and form the corresponding carboxylate anions of the higher fatty acid. Suitable alkaline reacting agents, therefore, include alkali and alkali earth metal hydroxides, ammonium hydroxides, aluminum hydroxide, cobaltous hydroxide and the like, alkali metal hydroxide, especially sodium and potassium hydroxide, being especially preferred. The quantity of such alkaline reacting agents can vary widely, but they will generally be introduced in an amount of from about 0.5 to 2.0 moles, preferably from about 0.8 to 1.4 moles, of the alkaline reacting agent per mole of the higher fatty acid which is introduced to zone 80.

The organic solvent fed to zone 80 via conduit 82 can comprise any of the organic solvents which have been mentioned above as being suitable for use in second extracting zone 50. Preferably, the organic solvent introduced to contacting zone 80 corresponds to the organic solvent selected for use in high pressure extraction zone 50. Thus, especially preferred are organic solvents selected from the group consisting of U.O.P. olefins, the feed olefins employed in the hydroformylation reaction, hydroformylation product, the heavy oxygenated bottoms fraction from the distillation of the oxo alcohols formed by hydrogenation of the hydroformylation product and mixtures thereof.

The conditions of temperature and pressure which are employed in contacting zone 80 are not critical and can vary widely. Generally, a temperature from about 5° to 90° C., preferably from about 20° to 50° C. will be employed. Pressures are not critical, and pressures of from 1 to 2 atmospheres can be employed. However, temperatures and pressures outside these ranges are entirely suitable. The manner in which the aqueous raffinate, organic solvent, alkaline reacting agent and higher fatty acid are contacted in zone 80 is also not critical. Thus, these streams can be contacted in a batchwise, semi-continuous or continuous manner in any conventional equipment, e.g., a stirred reaction vessel.

The reaction time provided in contacting zone 80 can also vary widely, and will generally range from about 15 minutes to 3 hours, preferably from about 30 to 60 minutes.

In the embodiments that are illustrated in the accompanying drawings, separate introduction of the alkaline reacting agent and a higher fatty acid are shown. It will, however, be understood that the selected alkaline reacting agent and higher fatty acid can be first admixed, as for example in a separate reaction vessel, and then fed as a combined stream (not shown) to contacting zone 80.

The amount of organic solvent which is introduced to contacting zone 80 can vary widely and need only be that amount which is sufficient to dissolve the cobaltous higher fatty acid salts which are formed therein. Generally, the organic solvent is introduced in an amount of from about 1 to 100 volumes, preferably from about 10 to 50 vols., per vol. of higher fatty acid which is introduced to zone 80.

In contacting zone 80 there are formed two liquid phases which can be separated and recovered by conventional means. The separated organic phase contains the cobaltous higher fatty acid salts which are formed, e.g., cobaltous oleate, in addition to any excess higher fatty acid and can be withdrawn via conduit 88 for recycle to the oxo reactor 10, as for example via conduit 6. The recycled organic solution of the cobaltous salt is generally referred to as a "cobalt soap." The separated aqueous phase contains the water soluble salts, such as sodium acetate, which are formed therein. Desirably, the separated aqueous phase is substantially free of dissolved cobalt values. Generally, therefore, the concentration of dissolved cobalt values in the separated aqueous phase is less than about 10 ppm.

Figure 2:
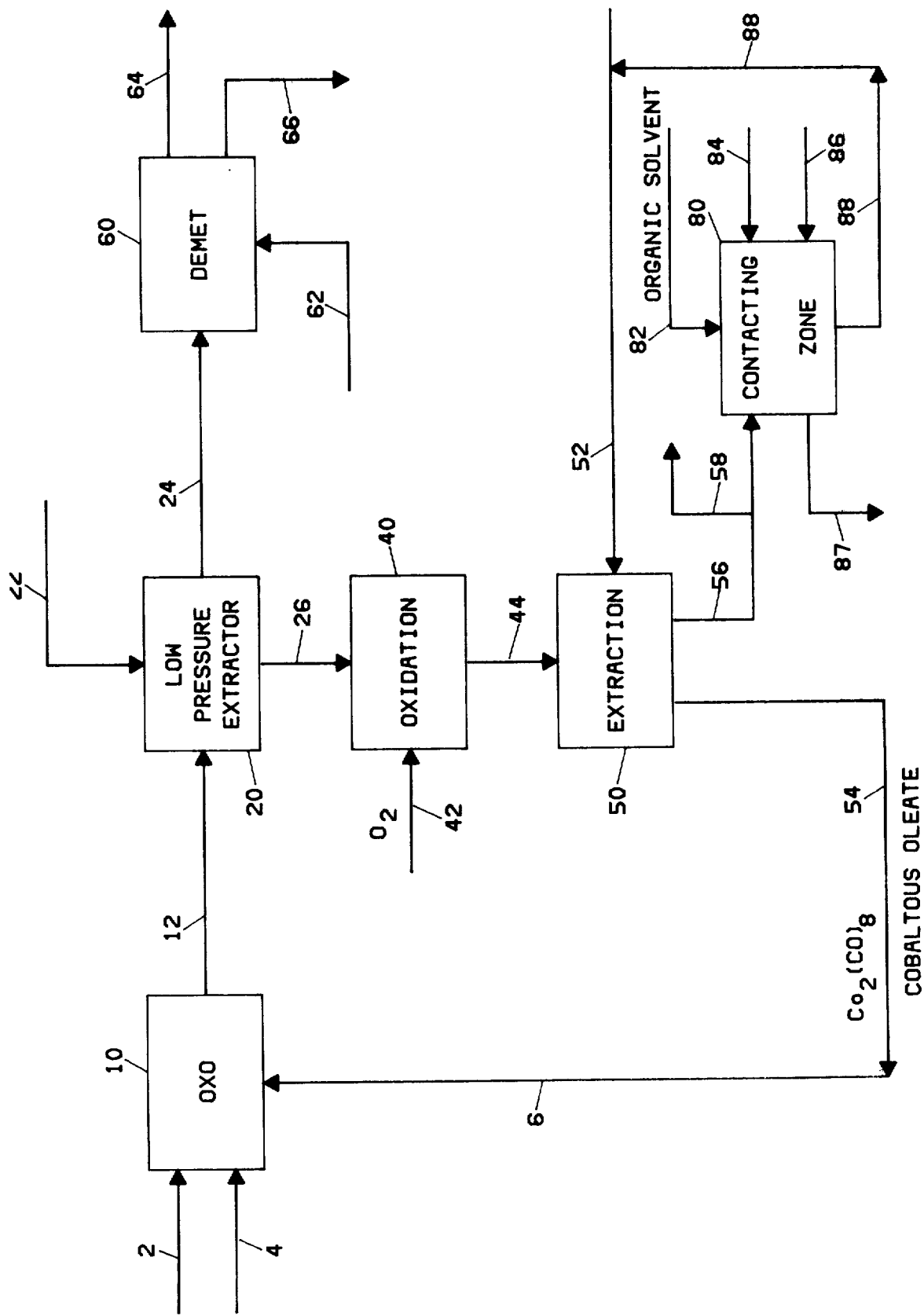
FIG. 2 is a diagrammatic illustration of a second embodiment of the process of this invention.

Referring now to the embodiment illustrated in FIG. 2, the organic phase formed in contacting zone 80 and containing the cobalt soap, is passed via conduit 88 to conduit 52 and thereby comprises at least a portion of the organic solvent which is introduced to second extraction zone 50. Therein, the thus-recycled organic phase functions to extract dicobalt octacarbonyl values which are present in the aqueous slurry of the dicobalt octacarbonyl introduced to zone 50 via conduit 42.

If desired, a portion of the organic phase in conduit 88 can be passed to conduit 6 as described above.

In this embodiment, the organic phase withdrawn from second extractor 50 via conduit 54 comprises a mixture of dicobalt octacarbonyl and the cobaltous higher fatty acid salt. The aqueous phase recovered from extractor 50 via conduit 56 can, as has been above described, be partially recycled via conduit 58 and the remainder fed to contacting zone 80, wherein it is admixed with organic solvent, alkaline reacting agent and higher molecular weight fatty acid, as described above, to form the cobaltous higher fatty acid salt from the cobaltous water soluble salt, e.g., cobaltous acetate, present in the aqueous phase in conduit 56.

Figure 3:
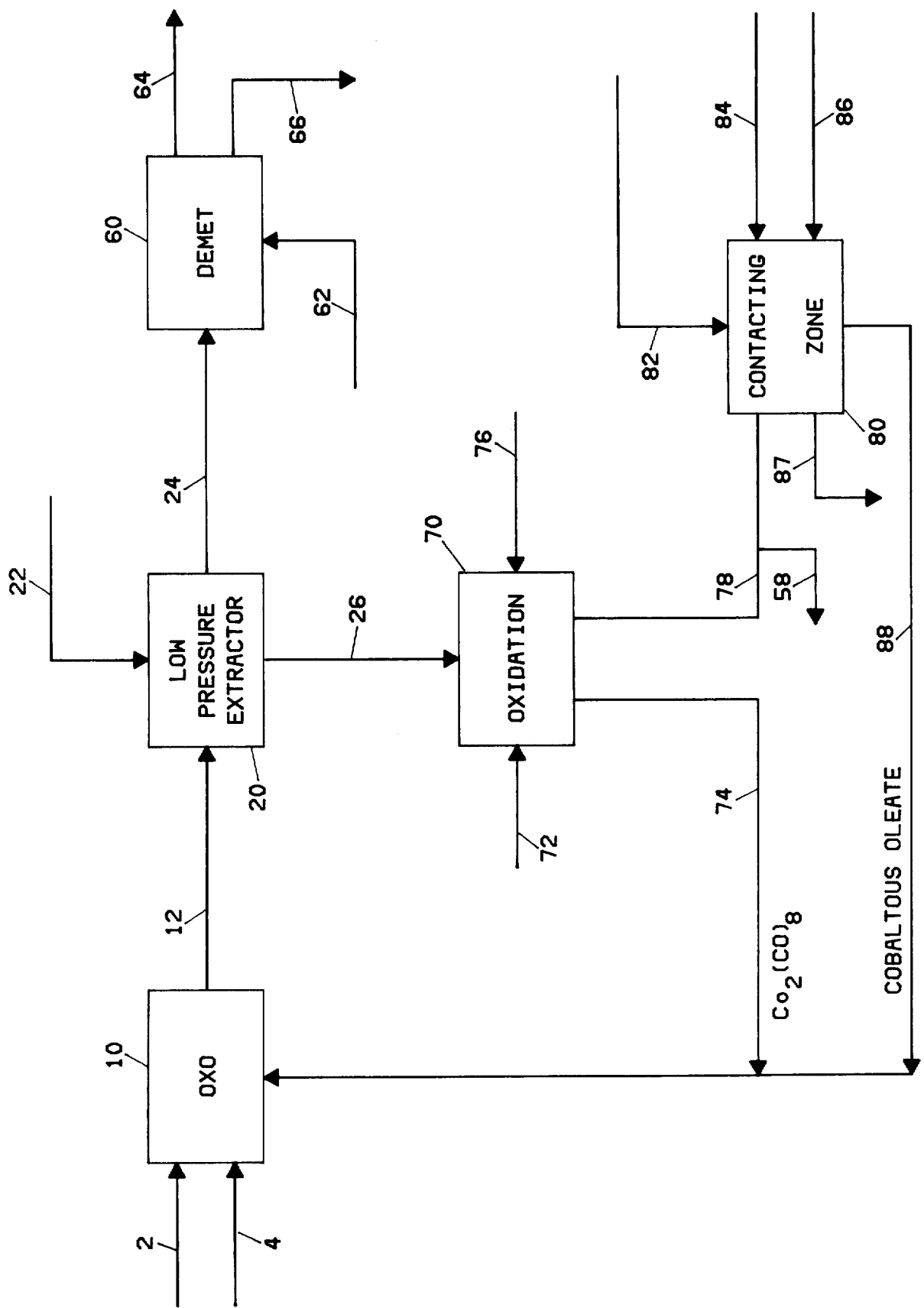
FIG. 3 is a diagrammatic illustration of a third embodiment of the process of this invention.

Another embodiment of the process of this invention is illustrated in FIG. 3, in which the aqueous extract containing $Co[Co(CO)_4]_2$, together with any excess cobaltous salt, e.g., cobaltous acetate, is withdrawn therefrom via conduit 26 and passed to oxidation zone 70 wherein the aqueous solution is contacted with an oxygen-containing gas, introduced thereto via conduit 72, and an organic solvent, introduced thereto via conduit 76, in order to effect simultaneous oxidation of the cobaltous bis-(tetracarbonylcobaltate) to form dicobalt octacarbonyl which is then efficiently, and simultaneously extracted into the organic solvent phase. The conditions of temperature employed in zone 70 correspond to those useful in oxidation zone 40, as described above. Thus, a temperature of from about 0° to 90° C., preferably from about 10° to 50° C., is used. To effect the most efficient and complete extraction of the thus-formed dicobalt octacarbonyl, the pressure in zone 70 should range up to about 1500 psig, preferably from about 15 to 1000 psig, more preferably from about 50 to 300 psig. As in oxidation zones 40 of FIGS. 1 and 2, the residence time of the liquids in zone 70 can vary widely, but will generally range from about 5 seconds to 1 hour, and preferably from about 0.5 to 15 minutes.

The type and quantities of organic solvents useful in zone 70 in this embodiment correspond to the solvents and amounts described above as suitable for use in second extracting zone 50.

The organic and aqueous phases formed in zone 70 are then separated and the organic phase is withdrawn via conduit 74. The withdrawn organic phase contains dissolved dicobalt octacarbonyl and can be passed to conduit 6 for recycle to oxo reactor 10. The aqueous phase, containing dissolved, water-soluble cobaltous acid salt (e.g., cobaltous acetate), as above described, can be withdrawn from zone 70 via conduit 78 and, as before, a portion thereof can be recycled via conduit 58 to conduit 22 or to intermediate storage, and the remaining portion passed to contacting zone 80. In contacting zone 80, the thus-fed aqueous phase is contacted with organic solvent, introduced thereto via conduit 82, alkaline reacting agents, introduced thereto via conduit 84, and higher molecular weight fatty acid, introduced thereto via conduit 86. The conditions of operation of contacting zone 80 and the quantities and identities of the materials charged thereto correspond to the above-discussed embodiments.

As before, the cobaltous higher fatty acid salt formed in contacting zone 80 is withdrawn via conduit 88 as an organic solution thereof and can be recycled to oxo reactor 10 as, for example, via conduit 6.

Figure 4:
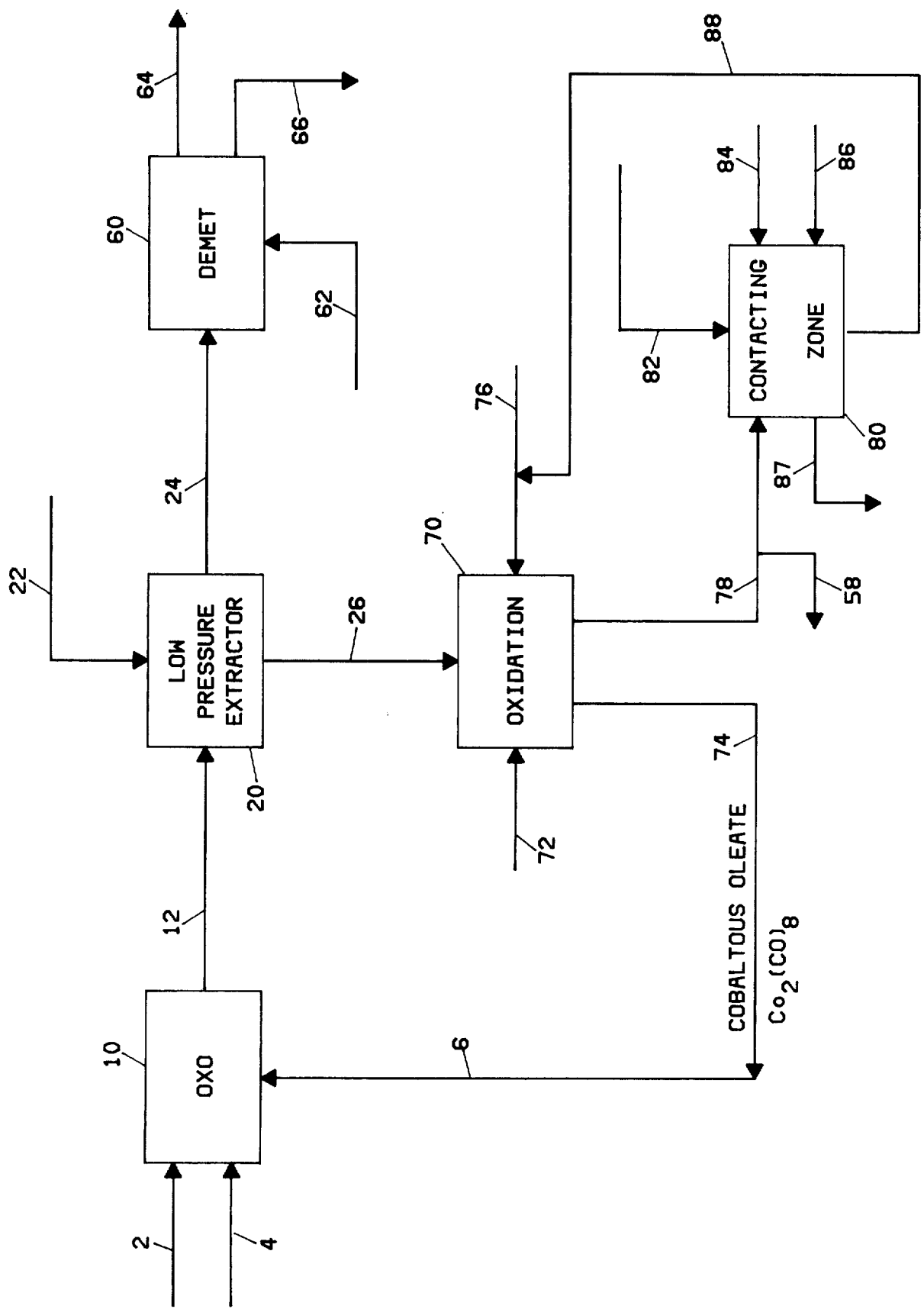
FIG. 4 is a diagrammatic illustration of a fourth embodiment of the process of this invention.

The embodiment illustrated in FIG. 4 also employs simultaneous oxidation and $Co_2(CO)_8$ extraction in oxidation zone 70. In this embodiment, the features of the simultaneous oxidation/extraction discussed above with respect to FIG. 3 are combined with the organic phase recycle feature of FIG. 2, in which at least a portion of the organic phase containing the cobaltous higher fatty acid in conduit 88 is passed to conduit 76 to provide the organic solvent feed to oxidation zone 70. In this embodiment, the organic phase withdrawn via conduit 74 contains dissolved dicobalt octacarbonyl and dissolved cobaltous higher fatty acid salt, e.g., cobaltous oleate, and is recycled via conduit 6 to the oxo reactor 10. The aqueous phase withdrawn from the high pressure oxidation zone 70 via conduit 78 comprises an aqueous solution of the cobaltous lower molecular weight acid, e.g., cobaltous acetate, and can be treated as described above with respect to FIG. 2 in contacting zone 80, with the provision of a recycle loop, indicated at conduit 58, if desired.

It has been surprisingly found that the yields of $Co_2(CO)_8$ in the oxidation zones of this invention (e.g., zones 40 and 70) can be significantly improved in the oxidation of the aqueous $Co(CO)_4^-$ values by charging gaseous carbon monoxide to the oxidation zone.

The gaseous CO can be introduced as CO or as a CO-containing gas, such as syn gas (mixtures of $H_2$ and CO), and can be introduced in any convenient manner, such as with either the oxygen-feed or via a separate conduit (not shown). Alternatively, the CO can be introduced via conduit 26 with the aqueous $Co(CO)_4^-$ values, which will then comprise a two-phase (gas/liquid) feed to the oxidation zone. The CO partial pressures in the oxidation zone 40 will generally range from about 10 to 4500 psig, and preferably from about 50 to 2000 psig, and the total pressure (sum of $CO+O_2$ partial pressures) will generally range from about 20 to 4500 psig, preferably from about 50 to 2500 psig. Preferably, mixtures of CO and oxygen-containing gas which are outside of the explosive range are employed. Thus, the volume percent CO in the total gas mixture for a CO/air mixture is preferably outside the range of 15.9 to 72.9 volume percent at one atmosphere total pressure, and outside the range of 18.4–62.0 volume percent at 10 atmospheres total pressure, such explosive ranges being taken from the International Critical Tables, Volume 2, pages 172–190 (McGraw Hill; 1927).

It will be understood from the above discussion that the extraction in zone 50 and the reactions performed in zone 80 of FIGS. 1 and 2 can be effected in a single vessel, herein termed "combined extraction/contacting vessel" (not shown), to which is fed the aqueous slurry of dicobalt octacarbonyl via conduit 44 for contact therein with the organic solvent for $Co_2(CO)_8$, a higher molecular weight fatty acid, and an alkaline reacting agent in order to form an organic phase containing a mixture of the dicobalt octacarbonyl and the cobaltous salt of the selected higher molecular weight fatty acid, which can then be recycled to the oxo reactors (e.g., stream 54 in the embodiment of FIG. 2). There is also produced in this extraction/contacting zone an aqueous stream (e.g., stream 87 in FIGS. 1 and 2) which can be recovered and is desirably substantially free of dissolved cobalt values. The temperature of the combined extraction/contacting step is preferably within the range of from about 0° to 90° C., and the pressure therein is preferably from about 15 to 1500 psig.

Similarly, it will be understood that the oxidation performed in zone 70 and the contacting performed in zone 80 of the embodiments of FIGS. 3 and 4 can be carried out in a single vessel, herein termed the "combined oxidation/contacting zone," to which the aqueous tetracarbonylcobaltate anion solution is fed via conduit 26, together with the organic solvent for dicobalt octacarbonyl and an oxygen-containing gas, and optionally a carbon monoxide-containing gas to increase the yield of dicobalt octacarbonyl therein as described above. Also passed to this combined oxidation/contacting zone is the higher molecular weight fatty acid and the alkaline reacting agent, to form therein an organic phase containing dissolved dicobalt octacarbonyl and cobaltous salt of the selected higher fatty acid (e.g., stream 74 in the embodiment of FIG. 4) which can then be recycled to the oxo reactors. A waste stream (e.g., stream 87 in the embodiments of FIGS. 3 and 4) is also formed which is desirable substantially free of cobalt values.

The temperatures and pressures in the combined oxidation/contacting zone will also range from about 0° to 90° C. and from about 15 to 1500 psig.

In a further embodiment, stream 26 in any of the above embodiments of this invention, containing the tetracarbonylcobaltate salt (e.g., $Co_2[(CO)_4]_2$) and excess $Co^{++}$ cations (e.g., cobaltous acetate), in addition to free organic or inorganic water-soluble acid, e.g., acetic acid, can be passed to a preforming zone to which CO and $H_2$ gas (e.g., synthesis gas) is supplied and wherein the aqueous solution is treated at a temperature of from about 0° to 200° C. and at a syn gas pressure of from 1500 to 4500 psig to form additional quantities of thetetracarbonylcobaltate anion from the excess cobaltous anion in stream 26. The syn gas composition is not critical and will generally contain from about 40 to 60 vol. % CO and from about 60 to 40 vol. % $H_2$. A heterogeneous catalyst can be employed such as activated charcoal, zeolite, basic ion exchange resins or the like. The treated aqueous phase which is withdrawn from the preforming zone can be then passed to the oxidation zones of the abovedescribed embodiments of this invention for increased yields therein of dicobalt octacarbonyl formed by oxidation of the tetracarbonylcobaltate values passed to said oxidation zone.

The process of this invention can be further illustrated by the following examples wherein parts are by weight unless otherwise indicated. In the Examples, analysis for $Co[Co(CO_4]_2$ is by EDTA titration of a sample whose total cobalt is oxidized to the $Co^{+2}$ form by use of $H_2O_2$. Concentrations of $Co[Co(CO)_4]_2$ are calculated on the basis of $Co(CO)_4^-$ anion determined by analyzing the CO gas released upon oxidation of the samples with an excess of potassium triiodide. $Co_2(CO)_8$ concentrations are calculated on the basis of elemental cobalt. Concentrations of cobaltous acetate are calculated on the basis of ethylene diamine tetraacetic acid titration. Yields and conversions of $Co_2(CO)_8$ are calculated on the basis of $Co[Co(CO)_4]_2$ consumed.

EXAMPLE 1

A 300 cc steel autoclave fitted with inlet and outlet valves is evacuated to a pressure of 0.1 Torr, and then charged with 52.9 grams of an aqueous solution containing 2.07 wt. % of Co as cobaltous bis-tetracarbonylcobaltate, 0.30 wt. % of Co as cobaltous acetate, 4.5 wt. % of acetic acid, and 57.3 grams of 1-dodecane. The charged aqueous solution therefore contains 1.38 wt. % cobalt as tetracarbonylcobaltate anion and 0.99 wt. % cobalt as cobaltous cation. The autoclave is then pressurized with 150 psig air and is maintained at 20° C. for 2.5 minutes while vigorously rocking the autoclave to thoroughly agitate the aqueous and organic phases. At the end of this time, the vessel is vented and the liquid discharged into a 500 cc separatory funnel under 1 atm. of nitrogen. The aqueous and organic phases are allowed to separate for 2 minutes and the aqueous phase is recovered and contacted under 1 atm. nitrogen with 15 grams of fresh 1-dodecene liquid to insure complete removal of dicobalt octacarbonyl therefrom. The resulting organic phase from this fresh 1-dodecene extraction is then combined with the organic phase obtained from the separatory funnel and passed to an oxo hydroformylation reaction to provide the feed of cobalt catalyst thereto in the form of the dicobalt octacarbonyl dissolved in the organic phase. The aqueous phase separated following the second extraction with the fresh 1-dodecene is determined to weigh 56.1 grams and to contain 1.52 wt. % cobalt as cobaltous cation and no detectable cobalt as tetracarbonylcobaltate anion. Thus, the yield of dicobalt octacarbonyl from the tetracarbonylcobaltate anion in the oxidation reaction is found to be about 62% at a conversion of about 100%.

The recovered aqueous phase is treated at about 66° C. with 10 cc of water which contains 1.2 grams of dissolved sodium hydroxide and 50 cc of 1-dodecene which contains 7.8 grams of oleic acid. The aqueous and organic phases are contacted at atmospheric pressure in a glass vessel and are stirred to provide complete mixing of the two liquid phases, for a period of 15 minutes while maintaining the 66° C. temperature. Thereafter, the two phases are cooled to room temperature and separated. The recovered aqueous phase is found to be essentially free of cobalt values and the organic phase is found to contain 0.85 gram of Co as cobaltous oleate. This organic phase containing cobaltous oleate is combined with the organic phase obtained as above containing dicobalt octacarbonyl for feed to a oxo hydroformylation reaction wherein the dodecene is hydroformylated to the corresponding $C_{13}$ aldehyde in the presence of CO and $H_2$ (40:60 CO:$H_2$ vol. ratio), at a pressure of 3500 psig and at a temperature of 175° C.

EXAMPLE 2

The 300 cc vessel in Example 1 is evacuated to a pressure of 0.1 Torr and charged with 60.0 grams of an aqueous solution containing 0.77 wt. % Co as cobaltous bis-tetracarbonylcobaltate, 0.16 wt. % Co as cobaltous acetate and 5.7 wt. % free acetic acid. The aqueous solution so charged thus contains 0.51 wt. % cobalt as tetracarbonylcobaltate anion and 0.42 wt. % cobalt as cobaltous cation. The vessel is then pressurized with 150 psig of air and agitated as in Example 1 for 5 minutes at 25° C. At the end of this time, the gases in the reaction vessel are vented and the liquid is discharged as an aqueous slurry of solid dicobalt octacarbonyl into a 500 cc separatory funnel blanketed with nitrogen (1 atm.). 1-Dodecene (50 cc; 37.9 grams) is then added to the aqueous slurry and agitated to dissolve all of the dicobalt octacarbonyl into the organic phase. After allowing the aqueous and organic phases to settle for two minutes, an aqueous phase is recovered and then washed with 15 grams of a fresh 1-dodecene charge in a separate glass vessel. The resulting fresh 1-dodecene organic extraction phase is then combined with the organic phase obtained from the separatory funnel.

The resulting aqueous phase is found to contain 0.62 wt. % cobalt as cobaltous cation and no detectable cobalt as tetracarbonylcobaltate anion. Thus, the yield of dicobalt octacarbonyl from the tetracarbonylcobaltate anion is about 61% at a conversion of about 100%. This aqueous phase is treated as described in Example 1 with 0.54 grams of sodium hydroxide in 10 cc of water and 3.7 grams of oleic acid in 30 cc of 1-dodecene. The resulting organic phase contains 0.37 gram Co as cobaltous oleate and is then recovered and combined with the above-described combined organic phase containing the dicobalt octacarbonyl.

This combined cobaltous oleate/dicobalt octacarbonyl organic phase containing 1-dodecene is then charged to the oxo hydroformylation reaction described in Example 1 for hydroformylation of the olefin in the presence of gaseous carbon monoxide and hydrogen to form the corresponding $C_{13}$ aldehyde.

Examples 1 and 2 are repeated in a series of runs except that the liquid organic extractant comprises hexenes, octenes, nonenes, toluene, hexane, dodecane and a heavy fraction, having the below-indicated composition (obtained by distillation of alcohol hydroformylation product), and similar results are obtained.

Heavy Fractionation Composition

About 25 wt. % esters of $C_{10}$ acids and $C_{10}$ alcohols, about 20–25 wt. % $C_{20}$ esters from $C_{20}$ alcohols and about 45–55 wt. % $C_{20}$ alcohols from $C_{10}$ aldehyde aldol condensation and hydrogenation.

It will be obvious that various changes and modifications may be made without departing from the invention and it is intended, therefore, that all matter contained in the foregoing description shall be interpreted as illustrative only and not limitative of the invention.

What is claimed is:

1. A process for demetalling an oxo product contaminated with cobalt-containing catalyst residues and recovering cobalt carbonyls therefrom which comprises:
   (a) treating the oxo product in a first demetalling zone with a first aqueous solution of a $Co^{++}$ salt of an organic or inorganic acid to extract at least a portion of the cobalt-containing catalyst residues from the oxo product into a first aqueous phase and to form products including said $Co^{++}$ salt and $Co[Co(CO)_4]_2$ therein;
   (b) substantially completing the demetalling of the thus treated oxo product by treatment in a second demetalling zone with an aqueous organic or inorganic acid in the presence of oxygen to form a $Co^{++}$ salt of said acid;
   (c) contacting said first aqueous phase in an oxidation zone with molecular oxygen-containing gas at a temperature of from about 0° to 90° C. to form $Co_2(CO)_8$;
   (d) contacting the oxidized aqueous mixture of step (c) with an organic solvent at elevated pressure to extract said $Co_2(CO)_8$ and to thereby form an organic extract containing said $Co_2(CO)_8$ and an aqueous raffinate substantially free of $Co_2(CO)_8$ and containing dissolved $Co^{++}$ acid salt values;
   (e) passing said organic extract to an oxo reaction zone as catalyst; and
   (f) contacting at least a portion of said aqueous raffinate with a higher molecular weight fatty acid, an organic solvent therefor and an alkaline reacting agent to form an organic phase containing the corresponding $Co^{++}$ higher fatty acid salt suitable for recycle to an oxo reaction zone as catalyst.

2. The process according to claim 1 wherein the pressure in the oxidation zone is in the range of from about 15 to 1500 psig.

3. The process of claim 1 wherein steps (c) and (d) are combined and wherein said oxidation is effected in the presence of said organic solvent.

4. The process according to claim 1 in which at least a portion of the aqueous raffinate from the extraction with the organic solvent in step (d) is passed to the first demetalling zone.

5. The process according to claim 1 in which said $Co^{30+}$ salt is cobalt acetate, cobalt formate or mixtures thereof.

6. The process according to claim 1 in which the organic solvent is selected from the group consisting of the feed olefins, hydroformylation product, the heavy oxygenated bottoms fraction from the distillation of oxo alcohols and mixtures thereof.

7. The process according to claim 6 in which the organic solvent is a portion of the feed olefins.

8. The process according to claim 1 in which the extraction with the organic solvent is carried out in the presence of CO gas at a pressure in the range of about 10 to about 2500 psig at a temperature of 0° to about 180° C., and with from about 0.1 to 10 volumes of the organic solvent per volume of said oxidized aqueous mixture so contacted.

9. The process according to claim 1 in which at least a portion of the organic phase containing said corresponding $Co^{++}$ higher fatty acid salt produced in step (f) is passed as recycle to step (d) in order to provide at least a portion of said organic solvent required in step (d), to thereby form an organic extract containing said $Co^{++}$ higher fatty acid salt and said $Co_2(CO)_8$ suitable for recycle to an oxo reaction zone as catalyst.

10. A process for demetalling an oxo product contaminated with cobalt-containing catalyst residues and recovering cobalt carbonyls therefrom which comprises:
   (a) treating the oxo product in a first demetalling zone with a first aqueous solution of a $Co^{++}$ salt of an organic or inorganic acid to extract at least a portion of the cobalt-containing catalyst residues from the oxo product into a first aqueous phase and to form products including said $Co^{++}$ salt and $Co[Co(CO)_4]_2$ therein;
   (b) substantially completing the demetalling of the thus treated oxo product by treatment in a second demetalling zone with an aqueous organic or inorganic acid in the presence of oxygen to form a $Co^{++}$ salt of said acid;
   (c) contacting said first aqueous phase in an oxidation zone with molecular oxygen-containing gas at a temperature of from about 0° to 90° C. to form $Co_2(CO)_8$ in the presence of an organic solvent to extract said $Co_2(CO)_8$ and to thereby form an organic extract containing said $Co_2(CO)_8$ and an aqueous raffinate substantially free of $Co_2(CO)_8$ and containing dissolved $Co^{++}$ acid salt values;
   (d) passing said organic extract to an oxo reaction zone as catalyst; and
   (e) contacting at least a portion of said aqueous raffinate with a higher molecular weight fatty acid, an organic solvent therefor and an alkaline reacting agent to form an organic phase containing the corresponding $Co^{++}$ higher fatty acid salt suitable for recycle to an oxo reaction zone as catalyst.

11. The process according to claim 10 wherein the pressure in the oxidation zone is in the range of from bout 15 to 1500 psig.

12. The process according to claim 10 in which at least a portion of the aqueous raffinate obtained in step (c) is passed to the first demetalling zone.

13. The process according to claim 10 in which the oxidation and extraction of step (c) is effected in the presence of gaseous carbon monoxide at a total pressure of from about 10 to 2500 psig.

14. The process according to claim 10 wherein at least a portion of said organic phase containing the said $Co^{++}$ higher fatty acid salt produced in step (e) is passed to step (c) to provide at least a portion of the organic solvent required therein, to thereby form an organic extract containing said $Co_2(CO)_8$ and said $Co^{++}$ higher fatty acid salt suitable for recycle to an oxo reaction zone as catalyst.

15. The process for demetalling an oxo product contaminated with cobalt-containing catalyst residues and recovering cobalt carbonyls therefrom which comprises:
  (a) treating the oxo product in a first demetalling zone with a first aqueous solution of a $Co^{++}$ salt of an organic or inorganic acid to extract at least a portion of the cobalt-containing catalyst residues from the oxo product into a first aqueous phase and to form products including said $Co^{++}$ salt and $Co[Co(CO)_4]_2$ therein;
  (b) substantially completing the demetalling of the thus treated oxo product by treatment in a second demetalling zone with an aqueous organic or inorganic acid in the presence of oxygen to form a $Co^{++}$ salt of said acid;
  (c) contacting said first aqueous phase in an oxidation zone with molecular oxygen-containing gas at a temperature of from about 0° to 90° C. to form $Co_2(CO)_8$; and
  (d) contacting the oxidized aqueous mixture of step (c) in a combined extraction/contacting zone with an organic solvent at elevated pressure in the presence of a higher molecular weight fatty acid and an alkaline reacting agent to extract said $Co_2(CO)_8$ into the organic phase and to form the corresponding $Co^{++}$ higher fatty acid salt, thereby forming an organic extract phase containing said extracted $Co_2(CO)_8$ and said $Co^{++}$ higher fatty acid salt suitable for recycle to an oxo reaction zone as catalyst.

16. The process for demetalling an oxo product contaminated with cobalt-containing catalyst residues and recovering cobalt carbonyls therefrom which comprises:
  (a) treating the oxo product in a first demetalling zone with a first aqueous solution of a $Co^{++}$ salt of an organic or inorganic acid to extract at least a portion of the cobalt-containing catalyst residues from the oxo product into a first aqueous phase and to form products including said $Co^{++}$ salt and $Co[Co(CO)_4]_2$ therein;
  (b) substantially completing the demetalling of the thus treated oxo product by treatment in a second demetalling zone with an aqueous organic or inorganic acid in the presence of oxygen to form a $Co^{++}$ salt of said acid; and
  (c) contacting said first aqueous phase in a combined oxidation/contacting zone with molecular oxygen-containing gas at a temperature of from about 0° to 90° C. and in the presence of a higher molecular weight fatty acid, an organic solvent therefor, and an alkaline reacting agent to form an organic phase containing $Co_2(CO)_8$ and $Co^{++}$ higher fatty acid salt corresponding to said higher fatty acid, said organic phase being suitable for recycle to an oxo reaction zone as catalyst.

* * * * *